(12) United States Patent
Maor et al.

(10) Patent No.: US 7,687,065 B1
(45) Date of Patent: *Mar. 30, 2010

(54) GEL COMPOSITION FOR SKIN CARE AND PROTECTION AND A METHOD FOR PREPARATION THEREOF

(75) Inventors: Zeev Maor, Dead Sea (IL); Assia Kogan, Jerusalem (IL); Shlomo Magdassi, Jerusalem (IL); Shaul Yehuda, Dead Sea (IL)

(73) Assignee: Dead Sea Laboraories, Ltd., Mitzpe Shalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/582,522

(22) PCT Filed: Dec. 17, 1998

(86) PCT No.: PCT/IL98/00615

§ 371 (c)(1),
(2), (4) Date: Aug. 24, 2000

(87) PCT Pub. No.: WO99/33443

PCT Pub. Date: Jul. 8, 1999

(30) Foreign Application Priority Data

Dec. 28, 1997 (IL) .................................. 122776

(51) Int. Cl.
*A61K 8/02* (2006.01)
*A61K 33/00* (2006.01)

(52) U.S. Cl. .................. 424/401; 424/600; 424/677; 424/722; 514/781; 514/782; 514/783; 514/784; 514/844; 514/859; 514/944

(58) Field of Classification Search .................. 424/400, 424/401, 70.13, 74, 600, 725, 677, 722; 514/944 514/725, 781, 782, 783, 784, 844, 859
See application file for complete search history.

(56) References Cited

U.S. PATENT DOCUMENTS

| 4,253,993 | A | | 3/1981 | Ramsey, III et al. |
| 4,321,156 | A | | 3/1982 | Bushman |
| 4,603,005 | A | | 7/1986 | Chaussee |
| 4,749,563 | A | * | 6/1988 | Georgalas ............... 424/59 |
| 4,943,432 | A | | 7/1990 | Biener |
| 5,100,656 | A | | 3/1992 | Lang et al. |
| 5,340,571 | A | | 8/1994 | Grace |
| 5,922,764 | A | * | 7/1999 | Cantin et al. ............... 514/557 |
| 6,248,340 | B1 | * | 6/2001 | Maor et al. ............... 424/401 |
| 6,271,260 | B1 | | 8/2001 | Kahale et al. |

FOREIGN PATENT DOCUMENTS

| EP | 0 217 975 B1 | 4/1987 |
| EP | 0 739 621 A1 | 10/1996 |
| EP | 0 783 881 A2 | 7/1997 |
| FR | 2 242 971 A | 4/1975 |
| FR | 2242971 | 4/1975 |
| JP | 08 104607 A | 4/1996 |
| JP | 8113530 A | 5/1996 |
| JP | 8231382 A | 9/1996 |
| JP | 9291015 A | 11/1997 |
| WO | WO 97/16155 A2 * | 5/1997 |
| WO | WO 98/52515 | 11/1998 |

OTHER PUBLICATIONS

Machine Translation of JP 08-113530, published Jul. 5, 1996, Kyotaro et al.*
The Handbook of Cosmetic Science & Tech, Elsevier Advanced Tech, 1993*
Flick, E., Cosmetics Additives: An lndustrail guide, 1991, Noyes Publications, pp. 179-180.*
Kyotaro, H. et al. "Cosmetics characterized by blending seawater or its salt obtained from the Dead Sea", Apr. 23, 1996, JP8-104607 A, machine translation.*
Flick, E. Cosmetic Additives, Noyes Publications, 1991, pp. 409-411.*
Maor, et al., Dead Sea Mineral-Based Cosmetics - Facts and Illusions, Israel Journal of Medical Sciences, 32 (supp.3), 28-35 (1996).
Mao R, et al, Skin Sm oothing Effects ofDead Sea M imerals:Com parative Profibm etric Evaliation ofS kin Surface, InternatbnalJournalofC osm etic Science, 19:105-110.

* cited by examiner

*Primary Examiner*—Gina C Yu
(74) *Attorney, Agent, or Firm*—Browdy and Neimark, PLLC

(57) ABSTRACT

The present invention relates to a gel composition useful for skin care and protection comprising up to 80% w/w Dead Sea water (or similarly constituted water), solubilizers, gelling agents or viscosity modifiers and deionized water to complete up to 100%. Preferably, the composition is a clear liquid gel. The gel optionally comprises hydrophobic and/or hydrophilic active agents. In the composition of the present invention the hydrophobic active agents may be vegetable oils, free fatty acids or vitamins, or any combination thereof and the hydrophilic active agent may be humectants, α-hydroxy acids, anti irritant agents, plant extracts, moisturizing agents or hydrolyzed plant proteins or any combination thereof. The gel may further comprise antioxidants and fragrances.

14 Claims, No Drawings

GEL COMPOSITION FOR SKIN CARE AND PROTECTION AND A METHOD FOR PREPARATION THEREOF

This application is made pursuant to 35 U.S.C. §371 of international application number PCT/IL98/00615, filed Dec. 17, 1998, with a priority date of Dec. 28, 1997.

FIELD OF THE INVENTION

The present invention generally relates to a gel composition useful for skin care and protection, and to a method for its preparation. More specifically, the present invention relates to a novel liquid gel composition comprising up to 80% w/w Dead Sea water and hydrophobic or hydrophilic active agents, such as vegetable oils, free fatty acids, vitamins, humectants, α-hydroxy acids, anti irritant agents, plant extracts, moisturizing agents and hydrolyzed plant proteins, or any combination thereof.

The gel composition of the present invention provides a vehicle of highly concentrated Dead Sea minerals and active agents to the skin preferably in the form of a clear gel.

BACKGROUND OF THE INVENTION

The skin, which is composed of three layers differing in their cell types and special functions; an overlaying epithelial layer (epidermis), an underlying connective tissue matrix (dermis) and adipose tissue (hypodermis), is the largest organ in the body and serves as, inter alia, a protective barrier from the external environment, impeding the entry of microorganisms, absorption of radiation and loss of water.

Physiologists assume that specific ions from minerals play important roles, mainly in the metabolism of healthy skin, mainly as co factors in enzymatic regulation activities. For example, there are indications that $Mg^{+2}$ is a co factor for phosphate transferring enzymes and participates in cAMP/cATP regulation. $Ca^{+2}$ is thought to regulate cell membrane permeability and $K^+$ to enhance $CO_2$ transport. Also, $Zn^{+2}$ may participate as a co factor in cell proliferation enzymatic regulation. In some in vitro and in vivo tests magnesium bromide, magnesium chloride, and potassium bromide exhibited inhibition of skin cell proliferation after dermal application (Ma'or Z., Magdassi S., Efron D. and Yehuda S. (1996) *Israel Journal of Medical Sciences* 32 (supp. 3), 28–35).

Minerals are capable of restoring moisture due to their hygroscopic characteristics. Minerals, if absorbed into skin cells, may enhance intracellular water capacity, and add water to the skin tissue from within.

Minerals may be absorbed into the skin from brine, from a bath with dissolved salts, or from dermal application of a mineral rich preparation. The skin is a multilayered biomembrane with certain absorption characteristics. As a dynamic living tissue, its absorption parameters are susceptible to constant changes. When applying a cosmetic blend, the most relevant parameter is the concentration cascade between each specific dissolved ion, outside and inside the skin surface. During the absorption process, a partitioning of minerals from the vehicle to skin may occur. The nature of the vehicle, namely the type of cosmetic preparation (e.g. a lipophilic cream or a hydrophilic gel), is significant in determining the kinetics of the process of skin penetration.

About 4–5% of the human body is made up of minerals. Some skin disorders are related to a specific mineral shortage. It is assumed that specific ions from minerals play an important role in healthy skin metabolism.

The Dead Sea is the richest natural mineral source in the world, with a concentration of 32% (w/v) dissolved minerals and a unique composition.

The main elements found in Dead Sea water are chlorine, magnesium, sodium, calcium, potassium and bromine. For example, the concentration of chlorine in the Dead Sea is 224900 mg/l as opposed to 22900 in the Mediterranean and 19000 in typical ocean water. Magnesium is 44000 mg/l in the Dead Sea as opposed to 1490 and 1350 in the Mediterranean and ocean, respectively. Sodium is 40100 mg/l in the Dead Sea as opposed to 12700 and 10500 in the Mediterranean and ocean, respectively. Calcium is 17200 mg/l in the Dead Sea as opposed to 470 and 400 in the Mediterranean and ocean, respectively. Potassium is 7650 mg/l in the Dead Sea as opposed to 470 and 390 in the Mediterranean and ocean, respectively and bromine is 5300 mg/l in the Dead Sea as opposed to 76 and 65 in the Mediterranean and ocean, respectively.

Many people, after bathing in the Dead Sea's salty water, reported a "baby smooth skin" feeling, and it is well known that minerals from the Dead Sea, as sea water, sea bath salts or sea mud have cosmetic and therapeutic effects on the skin (for example see Ma'or Z. and Yehuda S. (1997) *International Journal of Cosmetic Science* 19:105–110). However, treatment with these minerals has several drawbacks. It may be quite expensive and inconvenient for patients to travel to the Dead Sea itself for receiving treatment, and bringing the minerals to the patient's home may prove to be inconvenient. Large amounts of mineral ingredients (10 kg Dead Sea mud or salts for each treatment) must be applied and the treatment may be messy (such as treatment with Dead Sea mud). Furthermore, domestic metal pipes may be corrosively attacked while taking a highly concentrated mineral bath.

Many Dead Sea cosmetic preparations sold today actually contain a very small amount of minerals due to technical difficulties in using the highly electrolyte concentrated Dead Sea solutions in cosmetic formulation and due to product stabilization.

The present invention offers a highly concentrated Dead Sea mineral gel which is a superior vehicle of minerals and hydrophobic and hydrophilic active agents that have beneficial effects on the skin, to the cosmetic preparations sold today.

The composition of the present invention has the benefits of treatment with Dead Sea minerals, but none of the drawbacks. It is easy and simple to use and, in contrast with the treatments used today, may be in prolonged contact with the skin, enhancing the beneficial effects of the Dead Sea minerals.

SUMMARY OF THE INVENTION

The present invention relates to a gel composition useful for skin care and protection comprising up to 80% w/w Dead Sea water, hydrophobic and/or hydrophilic active agents, solubilizers, gelling agents or viscosity modifiers and water to complete up to 100%. Preferably, the composition is a clear liquid gel.

In the composition of the present invention the hydrophobic active agents may be vegetable oils, free fatty acids or vitamins, or any combination thereof and the hydrophilic active agent may be humectants, α-hydroxy acids, anti irritant agents, plant extracts, moisturizing agents or hydrolyzed plant proteins or any combination thereof. The gel may further comprise antioxidants and fragrances.

The present invention further relates to a method for the preparation of the said composition, comprising;

a) heating the mixture of hydrophobic active agent and solubilizer to approximately 40° C. while mixing; adding a mixture, at room temperature, of 15% w/w water and 30.0% w/w Dead Sea water, and heating again to approximately 40° C. while mixing;

b) in a different receptacle mixing the remaining water, Dead Sea water and gelling agent and heating to approximately 60° C. while mixing, cooling to 40° C. after receiving a clear solution;

c) adding the product of step b) to the product of step a) while mixing, and cooling to room temperature.

According to specific requirements, a) may further comprise a prior step of adding antioxidants and/or fragrance to the hydrophobic active agent and solubilizer, and step b) may further comprise adding the hydrophilic active agent together with the gelling agent and the remaining water and Dead Sea water.

DETAILED DESCRIPTION OF THE INVENTION

These and other features and advantages of the invention will be apparent upon consideration of the following detailed description of the preferred embodiment of the inventions.

The present invention relates to a composition comprising up to 80% Dead Sea water, hydrophobic and/or hydrophilic active agents, solubilizers and gelling agents or any viscosity modifiers for care of skin conditions, such as wrinkles,—for retaining skin moisture, and for care of skin related diseases.

The nomeclature used in the present invention to describe agents and compounds used in the present compositions, is the INCI nomeclature.

Hydrophilic active agents which may be used in the composition of the present invention may be humectants, such as glycerin, glycereth-7 or 12 or 26, butylene glycol, propylene glycol, panthenol, sorbitol and sorbitan laureth, or α-hydroxy acids, such as citric acid, lactic acid, glycolic acid and malic acid or anti-irritant agents, such as allantoin, PEG-28 or PEG-82, glyceryl tollowate or plant extracts, such as *Aloe barbadensis* extract or gel, balm mint extract, *Calendula officinalis* extract, Fenugreek extract, *Ginseng* extract, Horse chestnut extract, Ivy extract, Jujube extract, *Matricaria* extract and Witch hazel extract, or moisturizing agents, such as sodium hyaluronate, sodium PCA, sodium lactate, glycolipids, ceramides, sphingolipids and phospholipids and hydrolyzed plant proteins, such as hydrolyzed soy protein, hydrolyzed silk protein, hydrolyzed wheat protein, and hydrolyzed rice protein.

Hydrophobic active agents which may be used in the composition of the present invention may be vegetable oils such as avocado oil, borage oil, evening primrose oil, jojoba oil, palm kernel oil, rosehip oil, sunflower oil and wheat germ oil, or free fatty acids that are useful as moisturizers, such as ascorbic acid, linoleic acid and linolenic acid, or vitamins useful for treating skin aging effects such as ascorbyl palmitate, retinol, retinyl acetate, retinyl palmitate, retinyl propionate, tocopheryl acetate and tocopheryl linoleate.

The gelling agents which may be used in the present invention are: Guar gum, hydroxyethylcellulose, hydroxypropyl methylcellulose, methylcellulose, magnesium aluminum silicate and xanthan gum, though any appropriate viscosity modifying substance may be used.

The solubilizers used in the present invention are nonionic compounds such as Tween-20 or 80, oleth-20, ceteth-20 and PEG-hydrogenated castor oils-36,40,60. In the present invention the term "Dead Sea water" relates to any water with a TDS (Total Dissolved Salt) value between 25% and 40%.

This value is typical for water in the Dead Sea, and varies slightly depending on the depth and location from which the water is taken.

The major constituents of Dead Sea Water referred to in the present invention, as assessed by a water analysis carried out by the Geological Survey of Israel, are:

| | |
|---|---|
| Calcium (Ca + 2) | 36000–40000 mg/l |
| Chloride (Cl−) | 320000–370000 mg/l |
| Magnesium (Mg + 2) | 90000–95000 mg/l |
| Potassium (K+) | 1300–1500 mg/l |
| Sodium (Na+) | 1500–2500 mg/l |
| Bromide (Br−) | 11000–12000 mg/l |

In the present invention the term "Dead Sea water" relates to saline water with a TDS value between 25% and 40% and having an ion composition in the ranges given above.

The composition of the present invention comprises Dead Sea water, hydrophobic or hydrophilic active agents, or any mixture thereof, gelling agents or any other viscosity modifiers, a solubilizer and water, preferably, deionized water.

The said composition may further comprise anti oxidants and fragrances. The antioxidants may be BHA, BHT, tocopherol, tetrasodium EDTA or any combination thereof and the fragrance may be synthetic fragrances or an aromatic oil such as lavender oil, patchouli oil and sandalwood oil or any combination thereof.

The basic formula of the composition of the present invention is:

| | |
|---|---|
| Dead Sea water | 30.0–80.0% w/w |
| solubilizer | up to 4.0% w/w |
| hydrophilic active agent | up to 3.0% w/w |
| gelling agent | 0.7–1.2% w/w |
| hydrophobic active agent | up to 0.8% w/w |
| fragrance | up to 0.4% w/w |
| anti oxidant | 0.05–0.2% w/w |
| deionized water | to complete to 100% w/w |

The present invention further relates to a method for the preparation of the said composition. The basic method comprises the following steps:

a) heating the mixture of hydrophobic active agent and solubilizer to approximately 40° C. while mixing; adding a mixture (at room temperature) of 15% w/w water and 30.0% w/w Dead Sea water, and heating again to approximately 40° C. while mixing;

b) in a different receptacle mixing the remaining Dead Sea water, water and gelling agent and heating to approximately 60° C. while mixing, cooling to 40° C. after receiving a clear solution;

c) adding the product of step b) to the product of step a) while mixing, and cooling to room temperature.

Further additions, to the basic formula of Dead Sea water, hydrophobic active agents, solubilizer and water, according to specific requirements, comprise a prior step of adding to the above mentioned step a) anti oxidants and/or fragrances together with the hydrophobic active agent and solubilizer, and step b) further comprises adding the hydrophilic active agent together with the gelling agent (or any other viscosity modifier) and the remaining water and Dead Sea water.

The composition prepared according to this method may be used as a substitute for bath salts, and the reported "baby smooth skin" feeling when using Dead sea water is achieved without having to use large amounts of salts, and without exposing the domestic pipes to the corrosive effect of these salts. The present composition offers the added benefit of being able to "wear" the composition on the skin for many hours, thus being exposed to the benefits of the Dead Sea minerals for a longer time, enhancing their action towards skin care and protection.

The method of the present invention achieves solubilizing a hydrophobic agent in water which is highly concentrated with salts. Furthermore, the composition of the present invention is unique in that it may be a clear, transparent gel.

Transparency of the gel has important esthetic benefits; the clear transparent product may be sold in a transparent package showing off the homogeneity of the product. Also, colored active agents may be added to the gel for beauty in an encapsulated form.

Therefore, the composition of the present invention provides a superior vehicle of highly concentrated Dead Sea minerals and hydrophobic or hydrophilic active agents to the skin in the form of an esthetically superior clear gel.

The said invention will be further illustrated by the following examples. These examples do not intend to limit the scope of the invention but to demonstrate and clarify it only.

EXAMPLES

The following formulas of the present composition were prepared, formed a gel and were found stable for 4 weeks at 45° C. Formula I formed a clear transparent gel (the nomenclature used in the following examples are INCI names):

| Formula I | |
|---|---|
| Dead Sea water | 75.0% w/w |
| oleth-20 | 3.0% w/w |
| glycereth-26 | 2.0% w/w |
| hydroxyethylcellulose | 0.8% w/w |
| vitamin E-acetate (tocopheryl acetate) | 0.3% w/w |
| lavender oil | 0.3% w/w |
| BHA | 0.1% w/w |
| deionized water | to complete to 100% |

| Formula II | |
|---|---|
| Dead Sea water | 50.0% w/w |
| oleth-20 | 2.0% w/w |
| glycerin | 3.0% w/w |
| hydroxyethylcellulose | 1.0% w/w |
| vitamin A-palmitate (retinyl palmitate) | 0.2% w/w |
| patchouli oil | 0.2% w/w |
| BHA | 0.1% w/w |
| deionized water | to complete to 100% |

| Formula III | |
|---|---|
| Dead Sea water | 30.0% w/w |
| oleth-20 | 4.0% w/w |
| glycereth-26 | 2.0% w/w |
| hydroxyethylcellulose | 0.8% w/w |
| vitamin E acetate | 0.6% w/w |
| sandalwood oil | 0.2% w/w |
| BHA | 0.1% w/w |
| deionized water | to complete to 100% |

It will be apparent to those skilled in the art that various modifications and variations can be made in the various embodiments of the invention without departing from the spirit or scope of the invention. Thus, it is intended that the present invention include modifications and variations that are within the scope of the appended claims and their equivalents.

What is claimed is:

1. A clear gel composition useful for skin care and protection comprising: 30% to 80% w/w actual Dead Sea water; a non-ionic solubilizer; a hydrophobic active agent; a gelling agent or viscosity modifier; and deionized water to complete to 100%, the components being present in amounts that in combination provide a clear gel; wherein the gelling agent or viscosity modifier is selected from the group consisting of: Guar gum, hydroxyethylcellulose, hydroxypropyl methylcellulose, methylcellulose, magnesium aluminum silicate, and xanthan.

2. The gel composition according to claim 1, wherein the solubilizer is selected from the group consisting of: POE 20 sorbitan monolaurate, polyethylene glycol ether of oleyl alcohol having 20 $CH_2OCH_2$ units, POE 20 sorbitan monooleate, polyethylene glycol ether of cetyl alcohol having 20 $CH_2OCH_2$ units and PEG-hydrogenated castor oils-36, 40 and 60.

3. The gel composition according to claim 1, further comprising an antioxidant.

4. The gel composition according to claim 3, wherein the antioxidant is selected from the group consisting of: butylated hydroxy anisole, butylated hydroxy toluene, tocopherol, and tetrasodium ethylenediamine tetra-acetic acid.

5. The gel composition according to claim 1, further comprising a hydrophilic active agent.

6. The gel composition according to claim 1, wherein the hydrophobic active agent is selected from the group consisting of: vegetable oils, free fatty acids, and vitamins.

7. The gel composition according to claim 6, wherein the hydrophilic active agent is selected from the group consisting of: humectants, α-hydroxy acids, anti-irritant agents, plant extracts, moisturizing agents and hydrolyzed plant proteins.

8. The gel composition according to claim 1, further comprising a fragrance.

9. The gel composition according claim 8, wherein the fragrance is a synthetic fragrance or an aromatic oil selected from the group consisting of: lavender oil, patchouli oil, and sandalwood oil.

10. The gel composition according to claim 2, wherein the hydrophobic active agent is selected from the group consisting of: vegetable oils, free fatty acids, and vitamins.

11. The gel composition according to claim 2, wherein the hydrophilic active agent is selected from the group consisting of: humectants, α-hydroxy acids, anti-irritant agents, plant extracts, moisturizing agents and hydrolyzed plant proteins.

12. The gel composition according claim 2, further including a fragrance that is a synthetic fragrance or an aromatic oil selected from the group consisting of: lavender oil, patchouli oil, and sandalwood oil.

13. The gel composition according to claim 3, wherein the solubilizer is selected from the group consisting of: POE 20 sorbitan monolaurate, polyethylene glycol ether of oleyl alcohol having 20 $CH_2OCH_2$ units, POE 20 sorbitan monooleate, polyethylene glycol ether of cetyl alcohol having 20 $CH_2OCH_2$ units, and PEG-hydrogenated castor oils-36, 40 and 60.

14. The gel composition according to claim 3, wherein the antioxidant is selected from the group consisting of: butylated hydroxy anisole, butylated hydroxy toluene, tocopherol, and tetrasodium ethylenediamine tetra-acetic acid.

* * * * *